United States Patent
Rossi et al.

(10) Patent No.: US 6,379,931 B1
(45) Date of Patent: Apr. 30, 2002

(54) CHIMERIC DNA/RNA RIBOZYMES CONTAINING PROPANEDIOL

(75) Inventors: John J. Rossi, Alta Loma; Piotr M. Swiderski, San Dimas, both of CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/634,918

(22) Filed: Aug. 9, 2000

Related U.S. Application Data

(60) Provisional application No. 60/148,339, filed on Aug. 12, 1999.

(51) Int. Cl.$^7$ .......................... C12P 19/34; C12Q 1/68; C07H 21/02; C07H 21/04; C07H 21/00
(52) U.S. Cl. ...................... 435/91.31; 435/6; 536/23.1; 536/23.72; 536/24.5; 536/25.3
(58) Field of Search ...................... 435/6, 91.31, 91.1, 435/91.5, 455; 536/23.1, 24.5, 25.3

(56) References Cited

U.S. PATENT DOCUMENTS

| | | | |
|---|---|---|---|
| 5,144,019 A | | 9/1992 | Rossi et al. .................... 536/27 |
| 5,149,796 A | | 9/1992 | Rossi et al. .................... 536/27 |
| 5,496,698 A | * | 3/1996 | Draper et al. .................. 435/6 |
| 5,500,357 A | * | 3/1996 | Taira et al. .............. 435/91.31 |
| 5,695,938 A | | 12/1997 | Rossi et al. .................... 435/6 |
| 5,700,923 A | * | 12/1997 | Goodchild et al. ........ 536/23.1 |
| 5,965,720 A | * | 10/1999 | Gryaznov et al. ......... 536/23.1 |
| 5,972,704 A | * | 10/1999 | Draper et al. ............... 435/375 |

FOREIGN PATENT DOCUMENTS

| | | |
|---|---|---|
| WO | WO 91/03162 | 3/1991 |
| WO | WO 94/13688 | 6/1994 |
| WO | WO 95/06764 | 3/1995 |
| WO | WO 96/15240 | 5/1996 |

OTHER PUBLICATIONS

Eugen Uhlmann et al., Antisense Oligonucleotides: A New Therapeutic Principle, Chemical Reviews, vol. 90, No. 4, Jun. 1990 pp. 543–584.*
Friz Benseler et al., Hammerhead like Molecules Containing Non–Nucleoside Linkers Are Active RNA Catalysts, J. Am. Chem. Soc., vol. 115, No. 18, 1993 pp. 8483–8484.*
B. Dropulić et al., "Functional Characterization of a U5 Ribozyme: Intracellular Suppression of Human Immunodeficiency Virus Type 1 Expression," Journal of Virology 66(3):1432–1441, (Mar. 1992).
M. Koizumi et al., "Design and Anti–HIV–1 Activity of Hammerhead and Hairpin Ribozymes Containing a Stable Loop," Nucleosides & Nucleotides 17(1–3):207–218, 1998.
Rossi, "Ribozymes, genomics and therapeutics," Chemistry and Biology, Feb. 1999, vol. 6, No. 2, R33–R37.
Rossi, "Making Ribozymes Work in Cells," Current Biology, 1994, vol. 4, No. 5, pp. 469–471.

Snyder et al., "Ribozyme–Mediated Inhibition of bcr–abl Gene Expression in a Philadelphia Chromosome–Positive Cell Line," Blood, vol. 8, No. 2, pp. 600–605, Jul. 15, 1993.
Frimerman et al., "Chimeric DNA–RNA Hammerhead Ribozyme to Proliferating Cell Nuclear Antigen Reduces Stent–Induced Stenosis in a Porcine Coronary Model," Circulation, 99;697–703 (1999).
Gu et al., "Ribozyme–Mediated Inhibition of Expression of Leukocyte–type 12–Lipoxygenase in P orcine Aortic Vascular Smoth Muscle Cells," Circ. Res., 77:14–20 (1995).
Heidenreich et al., "Hammerhead Ribozyme–mediated Cleavage of the Long Terminal Repeat RNA of Human Immunodeficiency Virus Type 1," J. Biol. Chem., vol. 267, No. 3, pp. 1904–1909 (1992).
Pieken et al. "Kinetic Characterization of Ribonuclease–Resistant 2'–Modified Hammerhead Ribozymes," Science, vol. 253, pp. 314–317 (1991).
Oaolella et al., "Nuclease resistant ribozymes with high catalytic activity," The EMBO Journal, vol. 11, No. 5, pp. 1913–1919 (1992).
Swiderski et al., "Polystyrene Reverse–Phase Ion–Pair Chromatographyt of Chimeric Ribozymes," Analytical Biochemistry, vol. 216, pp. 83–88 (1994).
Petrie et al., "An Improved CPG Support for the Synthesis of 3'–Amine–Tailed Oligonucleotides," Bioconjugate Chem., vol. 3, No. 1, pp. 85–87 (1992).
Friedmann, "Progress Toward Human Gene Therapy," Science, vol. 244, pp. 1275–1281 (1989).

(List continued on next page.)

Primary Examiner—Andrew Wang
Assistant Examiner—Jane Zara
(74) Attorney, Agent, or Firm—Rothwell, Figg, Ernst & Manbeck

(57) ABSTRACT

DNA-RNA-(Pr)$_n$-RNA-DNA ribozymes of formula III or IV:

| | |
|---|---|
| 5' Z-cugaugag-(Pr)$_n$-cgaaa-X 3' | III. |
| 3'X-aaagc-(Pr)$_n$-gaguaguc-Z-R-Z-cugaugag-(Pr)$_n$-cgaaa-X 3' | IV. | in which
  X and Z comprise DNA sequences that base pair with an RNA substrate at positions adjacent to an RNA cleavage site;
  cugaugag and cgaaa are catalytic RNA sequences;
  Pr is a spacer residue —P(O)(OH)—O—CH$_2$CH$_2$CH$_2$—O—; and
  R is a bridging residue —O—CH$_2$—C(CH$_2$OH)(CH$_3$)—CH$_2$—O—.

The ribozymes can be made on any DNA synthesizer using phosphoramidite chemistry, and are useful as therapeutic agents for treating viral or endogenous RNA-mediated diseases. Preferred ribozymes target a sequence in the U5 region of HIV-1.

7 Claims, 1 Drawing Sheet

OTHER PUBLICATIONS

Castanotto et al., "Exogenous Cellular Delivery of Ribozymes and Ribozyme Encoding DNAs," *Methods in Molecular Biology 1997*, vol. 74:Ribozyme Protocols, pp. 429–439; Edited by P.C. Turner, Humana Press Inc., Totowa, NJ.

Castanotto et al., "Inhibition of HIV by Ribozymes and Antisense Oligonucleotides," HIV: A Practical Approach, vol. 2, pp. 289–303; Edited by Karn, J., Oxford University Press.

Guntaka, "Transcription Termination and Polyadenylation in Retoviruses," *Microbiological Reviews*, vol. 57, No. 3, pp. 511–521 (1993).

Böhnlein et al., "Identification of a U5–Specific Sequence Required for Efficient Polyadenylation within the Human immunodeficiency Virus Long Terminal Repeat," *JOurnal of Virology*, vol. 63, No. 1, pp. 421–424 (1989).

\* cited by examiner

FIG. 1

```
5'gcuuaagccucaauaaagcu 3'
3' GAATTCGG   TTATTTCGA 5'
         a   c
         a   u
         a   g
         g   a
         c   u
         Pr  g
         Pr  a
         Pr  g
          Pr
```

CHIMERIC DNA/RNA RIBOZYMES CONTAINING PROPANEDIOL

CROSS REFERENCE TO RELATED APPLICATION

This application claims the benefit of provisional application Serial No. 60/148,339, filed Aug. 12, 1999.

BACKGROUND OF THE INVENTION

This invention relates to ribozymes, which are molecules containing catalytic RNA sequences that are capable of cleaving RNA sequences in a substrate.

U.S. Pat. No. 5,149,796 describes chimeric DNA-RNA-DNA-RNA-DNA ribozymes of formulas I and II:

3' X-aaag-Y-aguaguc-Z 5' (5' Z-cugauga-Y-gaaa-X 3')   I.

3' X-caaag-Y-aguaguc-Z 5' (5' Z-cugauga-Y-gaaac-X 3')   II.

in which X, Y and Z are DNA sequences and cugauga, gaaa and gaaac are catalytic RNA sequences. The flanking X and Z components may be any DNA sequences that allow base pairing with the substrate RNA at appropriate positions adjacent to the substrate cleavage site. Y may be any DNA sequence that base pairs inter se in the manner required for catalytic cleavage of the substrate by the RNA sequences.

The X and Z sequences may be substituted at the respective 3' and 5' ends with ligands to facilitate cell entry, targeting within the cell and ultimate stability of the catalysts.

The chimeric DNA-RNA-DNA-RNA-DNA ribozymes can be synthesized in known manner by commercially available DNA synthesizers.

The patent discloses specific chimeric ribozymes which are targeted to cleave HIV-1 RNA sequences and states that the chimeric ribozymes are administered by known delivery agents and systems such as liposomes, defective viral particles, viral capsids, and standard DNA/RNA transfective procedures.

SUMMARY OF THE INVENTION

This invention provides chimeric DNA-RNA-$(Pr)_n$-RNA-DNA ribozymes which are capable of binding and cleaving an RNA substrate and which comprise the sequences of formula III or IV:

5' Z-cugaugag-$(Pr)_n$-cgaaa-X 3'   III.

3'X-aaagc-$(Pr)_n$-gaguaguc-Z-R-Z-cugaugag-$(Pr)_n$-cgaaa-X 3'   IV.

in which

X and Z comprise DNA sequences of at least six 2'-deoxyribonucleotide residues or modified 2'-deoxyribonucleotide residues that base pair with the RNA substrate at positions adjacent to the RNA cleavage site;

cugaugag and cgaaa are RNA sequences in which c, u, g and a are, respectively, residues of the ribonucleotides cytidylic acid, uridylic acid, guanylic and adenylic acid or, in the case of c and u, modified residues of c and u in which 2'-hydroxy is replaced with 2'-methoxy or other uncharged group such as 2'-allyloxy or 2'-fluoro;

Pr is a residue —P(O)(OH)—O—$CH_2CH_2CH_2$—O— derived from the C3 spacer reagent 3-(4,4'-dimethoxytrityloxy)propane-1-[(2-cyanoethyl)-(N,N-diisopropyl)]-phosphoramidite;

n is at least 1, preferably 1–50, more preferably 2–10:

R is a residue —O—$CH_2$—C($CH_2OH$)($CH_3$)—$CH_2$—O— derived from the bridging reagent 2-(dimethoxytrityl-O-methyl)-2-methyl-1,3-bis-O-(2-cyanoethyl-N,N-diisopropylphosphoramidite)-propane.

Examples of modified deoxyribonucleotides which can be present in Z and X include phosphorothioates and methlyphosphonates. There is no upper limit on the length of Z and X, but they will generally be about 6–50 residues, preferably about 10–20 residues, more preferably about 12–15 residues.

Z and X can each be substituted at the respective 5' and 3' ends with ligands to facilitate cell entry, targeting within the cell, and stability of the ribozymes and to facilitate capture and detection in in vitro assays. Such ligands include other nucleotides, proteins, carbohydrates, lipids, steroid hormones, cholesterol, amino linkers, Pr spacers, dyes such as fluoroscein and rhodamine, capture reagents such as biotin, and others.

The ribozymes can be encapsulated into liposomes for delivery into cells in vitro or in vivo.

A specific ribozyme of the invention is:

5'AGCTTTATTcugaugag(Pr)$_4$cgaaaGGCTTAAG3'   (Seq. ID 1)

which contains 5'AGCTTTATTcugaugag3' (SED ID NO. 1) and 5'cgaaaGGCTTAAG3' (SEQ ID NO. 2)

where c, u, g and a are, respectively, residues of the ribonucleotides cytidylic acid, uridylic acid, guanylic acid and adenylic acid;

C, T, G and A are, respectively, residues of the 2'-deoxyribonucleotides deoxycytidylic acid, deoxythymidylic acid, deoxyguanylic acid and deoxyadenylic acid

FIGURE DESCRIPTION

FIG. 1. The ribozyme containing SEQ ID NO. 1 and SEQ ID NO. 2 is targeted to cleave an HIV-1 RNA in the U5 region, as illustrated in FIG. 1.

Ribozymes of this invention can be designed and used for the same purposes and in the same ways that other ribozymes are used, as disclosed in U.S. Pat. No. 5,149,796, cited above, and as reviewed in Rossi, "Ribozymes, genomics and therapeutics," *Chemistry and Biology*, February 1999, vol. 6, no. 2, R33–R37, which are incorporated herein by reference. Thus, ribozymes of the invention can be used in the field of functional genomics as tools for studying gene functions and identifying potential new therapeutic targets for the treatment of disease. They can also be designed and used to treat RNA-mediated diseases such as HIV-1 infection or other diseases associated with altered expression or mutant forms of a gene or genes, including genetic diseases linked to allelic polymorphisms, and various cancers such as chronic myelogenous leukemia, breast cancer, and bladder cancer.

For example, use of a DNA-RNA chimeric ribozyme to study the pathogenetic role of the bcr-abl gene in $Ph^1$+ leukemogenesis, and potentially to treat patients with $Ph^1$+ chronic myelogenous leukemia, is disclosed in Snyder et al., "Ribozyme Inhibition of bcr-abl Gene Expression," *Blood* 82:2:600–605 (1992). As another example, a DNA-RNA chimeric ribozyme targeted to cleave mRNA for proliferating cell nuclear antigen (PCNA), and its use to reduce stent-induced stenosis in a porcine model, is disclosed in Frimerman et al., *Circulation* 99;697–703 (1999). As another example, a DNA-RNA chimeric ribozyme targeted to cleave mRNA for leukocyte-type 12 lipoxygenase (12-LO), and its use to study the specific effects of the 12-LO gene pathway in vascular disease, is disclosed in Gu et al., *Circ. Res.* 77:14–20 (1995). Ribozymes of this invention having the same RNA-binding flanking sequences as the ribozymes of the Snyder et al., Frimerman et al., and Gu et al. papers can be synthesized and used for the purposes disclosed in those papers. The disclosures of those papers are incorporated herein.

These examples are not intended to limit the invention. A ribozyme of the invention can be designed and synthesized to target any RNA which contains an NUH target sequence, where N is any ribonucleotide (C, U, G or A) and H is A, C or U, in an accessible binding site. Methods for identifying accessible binding sites in RNA are discussed in the Rossi review article cited above.

DESCRIPTION OF THE FIGURE

FIG. 1 illustrates one chimeric ribozyme of the invention (Ribozyme 1, comprising SEQ ID NO. 1 and SEQ ID NO. 2) base paired to an HIV-1 RNA sequence in the U5 region (SEQ ID NO. 7). The RNA portion of the ribozyme and the RNA of the substrate are shown in lower case letters.

DETAILED DESCRIPTION OF THE INVENTION

In the ribozymes of this invention, represented by formulas III and IV above, X and Z comprise DNA sequences of at least six 2'-deoxyribonucleotide residues or modified 2'-deoxyribonucleotide residues that base pair with the RNA substrate at positions adjacent to the RNA cleavage site. The number of base pairs required for optimal ribozyme cleavage at different sites is variable and must be determined empirically for each specific site, because the stability of the ribozyme/substrate duplex will be affected by several factors including G-C content, temperature and RNA structure. (a) 12–14 base pairs is a good starting point, since it has been shown that <12 can result in poor binding and >14 can reduce turnover by slowing dissociation of ribozyme and cleavage product. (b) The inhibition that longer flanking sequences exert on product release may be overcome with the design of asymmetric ribozymes where the ribozyme/target pairing is extended on one side of the hybrid and shortened on the other, such that one of two cleavage products is bound to the ribozyme by only a few bases. Target specificity can be achieved with as few as 12 basepairs.

The chimeric ribozymes of this invention can be synthesized on any DNA/RNA synthesizer using standard phospormamidite chemistry. Chemical modifications can be readily included in the molecules. Modifications such as phosphorothioates and methylphosphonates are more resistant to nuclease degradation than unmodified oligonucleotides and do not interfere with RNA cleavage activity of the ribozymes. (Heidenreich et al., *J. Biol. Chem.* 267:1904–1909 (1992)) Several other chemical modifications introduced into ribozymes have also been shown to increase stability without impairing catalytic capability. The 2' ribose hydroxyl group renders RNA more sensitive to nucleases than DNA, and modifications of this group can increase ribozyme stability. Only the 2'-OH required for catalysis must be preserved. Ribozymes containing 2'-fluorocytidine and 2'-fluorouridine or 2'-aminouridines are considerably more stable in serum and maintain catalytic activity (Pieken et al., *Science* 253:314–317 (1991)). Modification of the 2'-OH in all but the 6 nucleotides of the ribozyme's conserved catalytic core to 2'-O-allyl gave similar results. (Paolella et al., *EMBO J.* 11:1913–1919 (1992))

Several chimeric DNA-RNA-$(Pr)_n$-RNA-DNA ribozymes of this invention were synthesized on Perseptive Biosystems DNA Synthesizr Expedite 8909 in the trityl-off mode.

Ports 1 through 4 were used for the following A, C, G and T 2'-deoxyribonucleoside phosphoramidites, which were purchased from Perseptive Biosystems.

5'-Dimethoxytrityl-N-benzoyl-deoxyadenosine-3'-[(2-cyanoethyl)-(N,N-diisopropyl)]-phosphoramidite 5'-Dimethoxytrityl-N-benzoyl-deoxycytidine-3'-[(2-cyanoethyl)-(N,N-diisopropyl)]-phosphoramidite 5'-Dimethoxytrityl-N-p-tert-butylphenoxyacetyl-deoxyguannosine-3'-[(2-cyanoethyl)-(N,N-diisopropyl)]-phosphoramidite 5'-Dimethoxytrityl-thymidine-3'-[(2-cyanoethyl)-(N,N-diisopropyl)]-phosphoramidite Ports 5 through 8 were used for the following a, c, g and u ribonucleoside phosphoramidites, which were purchased from Peninsula.

5'-Dimethoxytrityl-N-benzoyl-adenosine, 2'-O-TBDMS-3'[(2-cyanoethyl)-(N,N-diisopropyl)]-phosphoramidite 5'-Dimethoxytrityl-N-benzoyl-cytidine, 2'-O-TBDMS-3' [(2-cyanoethyl)-(N,N-diisopropyl)]-phosphoramidite (or the 2'-O-methyl analog)

5'-Dimethoxytrityl-N-isobutyryl-guanosine, 2'-O-TBDMS-3'[(2-cyanoethyl)-(N,N-diisopropyl)]-phosphoramidite 5'-Dimethoxytrityl-uridine, 2'-O-TBDMS-3'[(2-cyanoethyl)-(N,N-diisopropyl)]-phosphoramidite.

Port 9 was used for C3 spacer (Pr) reagent, 3-(4,4'-dimethoxytrityloxy)propane-1-[(2-cyanoethyl)-(N,N-diisopropyl)]-phosphoramidite, purchased from Glen Research.

Tetraethylthiuram disulfide from Aldrich was used for thioation of two 3'-terminal phosphates of some of the synthesized probes.

3'-Aminopentyl CPG 500 Å was synthesized according to Petrie et al., *Bioconjugate Chemistry*, Vol. 3, No. 1 (1992).

After the synthesis oligonucleotide was deprotected with ethanolic ammonia (Swiderski P M, Bertrand E., Kaplan B E (1994) *Analytical Biochemistry*, 216, 83–86.

Deprotected ribozyme was purified by Polystyrene Reverse Phase Ion-Pair Chromatography (PRP-IPC) (Id.). Combined fractions containing the pure product were concentrated under reduced pressure to the volume of 1 ml. Sodium acetate (100 mg) and 2.5 ml of ethanol were added. Sample was kept at −20° C. for 4 hours and then centrifuged for 5 min. Supernatant did not have absorption at 260 nm. Precipitate was resuspended in 1 ml of sterile water and re-precipitated as above.

Preparative purification of oligonucleotides was carried out on a Gilson Gradient HPLC System equipped in Unipoint System Software. Purification was performed by Ion-Paired HPLC on polystyrene resin (PRP-1 (Hamilton) (4.6× 250 mm) buffer A, 50 mM acetate, 5 mM tetrabutylammonium phosphate in water (pH7.0); buffer B, 50 mM acetate, 5 mM tetrabutylammonium phosphate in water-acetonitrile 1:4, gradient 0–85% of B in 60 min.

The following ribozymes were synthesized as described above.

Ribozye 1

5'AGCTTTATTcugaugag(Pr)₄cgaaaGGCTTAAG3'
 which contains 5'AGCTTTATTcugaugag3' (SEQ ID NO. 1) and 5'cgaaaGGCTTAAG3' (SEQ ID NO. 2)

Ribozyme 2 (2'-O-methylated c and u)

5'AGCTTTATTc*u*gau*gag(Pr)₄cgaaaGGCTTA*A*G3'
 which contains 5'AGCTTTATTc*u*gau*gag3' (SEQ ID NO. 3) and
 5'cgaaaGGCTTA*A*G3' (SEQ ID NO. 4)

Ribozyme 3 (2'-O-methylated c and u, 5'-fluoresceine)

5' Fl-AGCTTTATTc*u*gau*gag(Pr)₄cgaaaGGCTTA*A*G 3'
 which contains 5'AGCTTTATTc*u*gau*gag3' (SEQ ID NO. 3) and
 5'cgaaaGGCTTA*A*G3' (SEQ ID NO. 4)

Ribozyme 4 (5'fluoresceine, 3'-amino linker)

5' Fl-Pr-TCACACAACAcugaugag (Pr)₄ cgaaaCGGGCACAC-Al 3'
 which contains 5'TCACACAACAcugaugag3' (SEQ ID NO. 5) and 5'cgaaaCGGGCACAC3' (SEQ ID NO. 6)

In ribozymes 1–4, c, u, g and a are, respectively, residues of the ribonucleotides cytidylic acid, uridylic acid, guanylic acid and adenylic acid; c* and u* are, respectively, residues of 2'-O-methylated analog of cytidylic acid and uridylic acid; C, T, G and A are, respectively, residues of the 2'-deoxyribonucleotides deoxycytidylic acid, deoxythymidylic acid, deoxyguanylic acid and deoxyadenylic acid; and A* is the residue of the thioated analog of deoxyadenylic acid. Pr has the meaning given above. Fl represents a fluoresceine residue and Al represents the amino linker pentylamine. Pentylamine was incorporated at the 3' end of ribozyme IV by carrying out the ribozyme synthesis on long chain alkylamine CPG (LCAA-CPG) from Sigma Chem., St. Louis, as described in Petrie et al., *Bioconjugate Chem.*, Vol. 3, No. 1 (1992), except that the pentylamine-CPG was used instead of the hexylamine-CPG illustrated in Petrie et al. Fluorescein was incorporated at the 5' end of ribozymes III and IV using fluorescein phosphoramidite from Glen Research as the last added reagent.

Ribozymes 1,2 and 3 are targeted to cleave HIV-1 in SEQ ID NO. XX of the U5 region, as illustrated in the Figure.

Bridged chimeric ribozymes of Formula IV can be made by the same process, utilizing the bridging reagent 2-(dimethoxytrityl-O-methyl)-2-methyl-1,3-bis-O-(2-cyanoethyl-N,N-diisopropylphosphoramidite)-propane as the last added reagent.

The bridging reagent was prepared as follows:

Synthesis of intermediate, 2-(dimethoxytrityl-O-methyl)-2-methyl-1,3-propanediol 2-Hydroxymethyl-2-methyl-1,3-propanediol (0.721 g, 6.0 mmole) was dissolved in 5 ml of dry pyridine and dimethoxytrityl chloride (0.9 g, 3.0 mmole) was added. The reaction mixture was kept at room temperature for 18 hours, concentrated to a syrup, dissolved in 200 ml of dichloromethane and washed with bicarbonate and brine (2×50 ml). The resultant solution was coevaporated with toluene (2×50 ml) and isopropanol (2×50 ml). The crude product was purified by flash chromatography on 12 g of silica gel H in gradient of 1%–3% of ethanol in dichloromethane. Sample for NMR was purified by flash chromatography on 2 g of silica gel H in gradient of 12–75% of ethyl acetate in hexane-triethylamine (95:5). Rf 0.28(C); Rf 0.55 (A3); MS 423.528.

Synthesis of bridging reagent, 2-(dimethoxytrityl-O-methyl)-2-methyl-1,3-bis-O-(2-cyanoethyl-N,N-diisopropylphosphoramidite)-propane 2-(dimethoxytrityl-O-methyl)-2-methyl-1,3-propanediol (1.5 g, 4.0 mmole) was dissolved in 5 ml dry acetonitrile and diisopropylethylamine (2.10 ml, 12.0 mmole) was added. Phosphine (2.13 g, 2.0 ml, 9.0 mmole, 1.12 eq. in 2.0 ml of THF) was added dropwise. After 2 hours the reaction was quenched with 1 ml of methanol, concentrated to syrup, dissolved in 200 ml of ethyl acetate, and then washed with bicarbonate and brine. The resultant solution was coevaporated with toluene (2×50 ml) to a syrupy residue. The crude product was purified on open column 35 g of silica gel H in a gradient of 4–50% of toluene in hexane. 2% of DEA was added to both solvents. The yield was 2.07 g (1.36 mmole, 70%). Rf 0.50(B); $^{31}$P NMR (300 Mhz, CdCl3) δ147.98, 146.56; MS 822.960.

Analytical polyacrylamide gel electrophoresis (PAGE) was carried out using 20% crosslinked gels (1 mm thick, 19:1 acrylamide:bis-acrylamide). Buffer 100 ml Tris-borate, 1 mM EDTA, 7 M urea, pH 8.3 (25). Gels were visualized by UV (254 nm) shadowing followed by methylene blue staining.

The bridged chimeric ribozymes of formula IV are made by synthesizing a ribozyme of formula III, then reacting the 5'-ends with the bridging reagent on the same synthesizer. Examples of specific bridged chimeric ribozymes which can be prepared in this way are:

Ribozyme 5

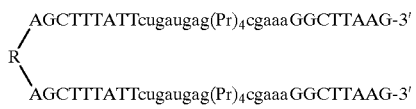

Ribozyme 6

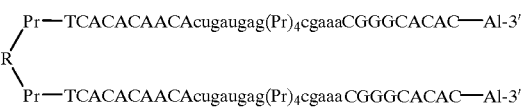

Ribozyme 5 contains SEQ ID NO. 1 and SEQ ID NO. 2. Ribozyme 6 contains SEQ ID NO. 5 and SEQ ID NO. 6.

Ribozymes of the invention can be administered through the use of liposomes. Liposomes protect the ribozyme against enzymatic attack and the liquid capsule of the liposome facilitates transfer through the cell wall. Liposomes which have been developed for delivery of other nucleic acids to cells (See, e.g., Friedmann, *Science*, 244:1275–1281 (1989)) can be used for delivery of the ribozymes of this invention into cells. Castanotto, Bertstrand and Rossi, "Exogenous Cellular Delivery of Ribozymes and Ribozyme Encoding DNAs," *Methods in Molecular Biology* 1997, vol. 74:Ribozyme Protocols, pages 429–439, Edited by Turner PG, Humana Press Inc., Totowa, N.J. The disclosures of the Friedmann and Castanotto et al. references relating to the preparation of liposomes and the use of liposomes to deliver ribozymes and other nucleic acids into cells in vitro and in vivo, are incorporated herein.

For therapeutic purposes liposomes containing ribozymes of the invention can be administered by intravenous or intramuscular injection. Liposomes containing a ribozyme designed to inhibit stent-induced re-stenosis can be administered by balloon catheterization. The ribozyme should be administered in a therapeutically effective amount. This amount for a particular patient can be determined by the treating physician, and will depend upon a number of factors, including the age, weight and sex of the patient, the disease and the stage of the disease being treated, and whether the ribozyme is being administered as sole therapeutic agent or as one of a combination of agents directed against the same disease.

What is claimed is:

1. A chimeric ribozyme of the formula III or IV

5' Z-cugaugag-(Pr)$_n$-cgaaa-X 3'    III

3'X-aaagc-(Pr)$_n$-gaguaguc-Z-R-Z-cugaugag-(Pr)$_n$-cgaaa-X 3'    IV in which
   X and Z comprise DNA sequences of at least six 2'-deoxyribonucleotide residues or modified 2'-deoxyribonucleotide residues that base pair with an RNA substrate at positions adjacent to the RNA cleavage site;
   cugaugag and cgaaa are RNA sequences in which c, u, g and a are, respectively, residues of the ribonucleotides cytidylic acid, uridylic acid, guanylic and adenylic acid or, in the case of c and u, modified residues of c and u in which 2'-hydroxy is replaced with 2'-methoxy or other uncharged group such as 2'-allyloxy or 2'-fluoro;
   Pr is a residue —P(O)(OH)—O—CH$_2$CH$_2$CH$_2$—O—;
   n is at least 1;
   R is a residue —O—CH$_2$—C(CH$_2$OH)(CH$_3$)—CH$_2$—O—.

2. A chimeric ribozyme of claim 1 in which n is in the range of 1 to about 50.

3. A chimeric ribozyme of claim 1 in which n is in the range of about 2–10.

4. A chimeric ribozyme of claim 1 having the formula:

5' AGCTTTATTcugaugag(Pr)$_4$cgaaaGGCTTAA G 3'.

5. A chimeric ribozyme of claim 1 having the formula:

5' AGCTTTATTcugaugag(Pr)$_4$cgaaaGGCTTA*A*G 3' wherein c and u are, respectively, residues of 2'-O-methylated analog of cytidylic acid and uridylic acid; and A* is the residue of the thioated analog of deoxyadenylic acid wherein S is bonded to P and is nonbridging between neighboring nucleotides.

6. A chimeric ribozyme of claim 5 having the formula:

5' Fl-AGCTTTATTcugaugag(Pr)$_4$cgaaaGGCTTA*A*G 3' wherein Fl represents fluoresceine.

7. A chimeric ribozyme of claim 1 having the formula:

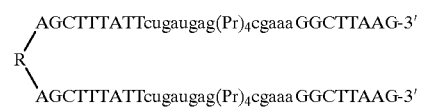

* * * * *

```
                         SEQUENCE LISTING

<160> NUMBER OF SEQ ID NOS:  7

<210> SEQ ID NO 1
<211> LENGTH: 17
<212> TYPE: DNA
<213> ORGANISM: Artificial Sequence
<220> FEATURE:
<223> OTHER INFORMATION: Description of Combined DNA/RNA Molecule:
      Residues 1-9 are DNA; residues 10-17 are RNA.
<223> OTHER INFORMATION: Description of Artificial Sequence:  Chimeric
      DNA/RNA ribozyme sequence

<400> SEQUENCE: 1
agctttattc ugaugag                                                17

<210> SEQ ID NO 2
<211> LENGTH: 12
<212> TYPE: DNA
<213> ORGANISM: Artificial Sequence
<220> FEATURE:
<223> OTHER INFORMATION: Description of Combined DNA/RNA Molecule:
      Residues 1-5 are RNA; residues 6-12 are DNA
<223> OTHER INFORMATION: Description of Artificial Sequence: Chimeric
      DNA/RNA ribozyme sequence

<400> SEQUENCE: 2
cgaaaggctt aa                                                     12

<210> SEQ ID NO 3
<211> LENGTH: 17
<212> TYPE: DNA
<213> ORGANISM: Artificial Sequence
<220> FEATURE:
<223> OTHER INFORMATION: Description of Combined DNA/RNA Molecule:
      Residues 1-9 are DNA; residues 10-17 are RNA.
      Residue 10 is cm.  Residues 11 and 14 are um.
<223> OTHER INFORMATION: Description of Artificial Sequence:  Chimeric
      DNA/RNA ribozyme sequence

<400> SEQUENCE: 3
agctttattc ugaugag                                                17

<210> SEQ ID NO 4
<211> LENGTH: 12
<212> TYPE: DNA
<213> ORGANISM: Artificial Sequence
<220> FEATURE:
<223> OTHER INFORMATION: Description of Combined DNA/RNA Molecule:
      Residues 1-5 are RNA; residues 7-12 are DNA.  Residues 11 and 12
      are the thioated analog of deoxyadenylic acid.
<223> OTHER INFORMATION: Description of Artificial Sequence:  Chimeric
      DNA/RNA ribozyme sequence

<400> SEQUENCE: 4
cgaaaggctt aa                                                     12

<210> SEQ ID NO 5
<211> LENGTH: 18
<212> TYPE: DNA
<213> ORGANISM: Artificial Sequence
<220> FEATURE:
<223> OTHER INFORMATION: Description of Combined DNA/RNA Molecule:
```

```
         Residues 1-10 are DNA; residues 11-18 are RNA.
<223> OTHER INFORMATION: Description of Artificial Sequence:  Chimeric
      DNA/RNA ribozyme sequence

<400> SEQUENCE: 5
tcacacaaca cugaugag                                                   18

<210> SEQ ID NO 6
<211> LENGTH: 14
<212> TYPE: DNA
<213> ORGANISM: Artificial Sequence
<220> FEATURE:
<223> OTHER INFORMATION: Description of Combined DNA/RNA Molecule:
      Residues 1-5 are RNA; residues 6-14 are DNA.
<223> OTHER INFORMATION: Description of Artificial Sequence:  Chimeric
      DNA/RNA ribozyme sequence

<400> SEQUENCE: 6
cgaaacgggc acac                                                       14

<210> SEQ ID NO 7
<211> LENGTH: 20
<212> TYPE: RNA
<213> ORGANISM: Human immunodeficiency virus

<400> SEQUENCE: 7
gcuuaagccu caauaaagcu                                                 20
```